United States Patent [19]

Nicolas-Morgantini et al.

[11] Patent Number: 5,954,871
[45] Date of Patent: Sep. 21, 1999

[54] COMPOSITE MELANIN PIGMENT IN THE FORM OF PARTICLES COMPRISING A WAX-BASED SPHERICAL CORE, PREPARATION PROCESSES AND COSMETIC USES

[75] Inventors: Luc Nicolas-Morgantini, Rully; Alain Lety, Lagny Sur Marne; Guy Vanlerberghe, Villevaude, all of France

[73] Assignee: L'OREAL, France

[21] Appl. No.: 08/991,303

[22] Filed: Dec. 16, 1997

[30] Foreign Application Priority Data

Dec. 16, 1996 [FR] France .................................. 96 15450

[51] Int. Cl.$^6$ ....................................................... C09D 4/00
[52] U.S. Cl. ........................... 106/502; 8/127.5; 8/127.51; 8/127.6; 8/405; 8/425; 106/498; 106/504; 106/506; 424/59; 424/60; 424/61; 424/70.1; 424/78.03; 424/401
[58] Field of Search ..................... 106/498, 502, 106/504, 506; 8/127.5, 127.51, 127.6, 405, 425; 424/59, 60, 61, 70.1, 78.03, 401

[56] References Cited

U.S. PATENT DOCUMENTS

| | | | |
|---|---|---|---|
| 5,244,497 | 9/1993 | Junino et al. | 106/498 |
| 5,380,359 | 1/1995 | Honda et al. | 106/414 |
| 5,449,403 | 9/1995 | Andrean et al. | 106/498 |
| 5,496,543 | 3/1996 | Lagrange et al. | 424/70.7 |
| 5,583,234 | 12/1996 | Lagrange et al. | 548/455 |
| 5,776,241 | 7/1998 | Giacomoni et al. | 106/498 |
| 5,849,278 | 12/1998 | Piot et al. | 424/70.7 |

FOREIGN PATENT DOCUMENTS

| | | |
|---|---|---|
| 0 441 689 | 8/1991 | European Pat. Off. . |
| 0 518 773 | 12/1992 | European Pat. Off. . |
| WO 93/12761 | 7/1993 | WIPO . |
| WO 93/13743 | 7/1993 | WIPO . |
| WO 93/13744 | 7/1993 | WIPO . |
| WO 93/13745 | 7/1993 | WIPO . |
| WO 93/19721 | 10/1993 | WIPO . |
| WO 94/25531 | 11/1994 | WIPO . |

OTHER PUBLICATIONS

Derwent Abstract of EP 0 518 773 (Dec. 1992).

*Primary Examiner*—Mark L. Bell
*Assistant Examiner*—Scott L. Hertzog
*Attorney, Agent, or Firm*—Finnegan, Henderson, Farabow, Garrett & Dunner, L.L.P.

[57] ABSTRACT

A composite melanin pigment in the form of particles comprising a spherical core less than 1 $\mu$m in diameter, which comprises at least one wax and at least one surfactant, and an outer layer which envelops the core, which comprises at least one compound resulting from the oxidative polymerization of a melanin pigment precursor; and uses of the pigment in powder form or in the form of an aqueous dispersion, in cosmetic compositions, in particular in dye products and/or make-up products and/or care products for keratin substances such as the skin, the hair and the nails.

59 Claims, No Drawings

COMPOSITE MELANIN PIGMENT IN THE FORM OF PARTICLES COMPRISING A WAX-BASED SPHERICAL CORE, PREPARATION PROCESSES AND COSMETIC USES

The present invention relates to a composite melanin pigment in the form of particles comprising a wax-based spherical core and an outer layer which envelops the core, comprising at least one compound resulting from the oxidative polymerization of a melanin pigment precursor, as well as to its uses in powder form or in aqueous dispersion form, in cosmetic compositions, in particular dye products and/or make-up products and/or care products for keratin substances.

Pigments based on metal compounds such as, for example, black and brown iron oxides, are generally used in make-up compositions for the skin and for the exoskeleton.

Novel pigment systems which can also be used in hair dye compositions, giving the hair a coloration which can be removed quickly, have been sought for some years.

Composite pigments consisting of colored inorganic particles less than 200 µm in size, containing inside them and/or at their surface a synthetic melanin pigment formed in situ by oxidation of an indole compound, are known from French patent application FR 2,686,345 (U.S. Pat. No. 5,449,403). Composite pigments consisting of inorganic or organic particles less than 200 µm in size, containing inside them and/or at their surface a synthetic melanin pigment formed in situ by oxidation of an indoline compound, are also known from French patent application FR 2,686,248 (U.S. Pat. No. 5,496,543).

The inventors have discovered, surprisingly, novel composite melanin pigments in the form of wax microparticles coated with a synthetic pigment formed in situ by oxidation of a melanin pigment precursor, which, on account of the extremely small size of the particles which constitute them, become better and more homogeneously distributed in cosmetic formulations, allow better spreading of the composition on the skin or the exoskeleton and have a higher covering power.

The inventors have observed, unexpectedly, that the composite melanin pigments of the invention also have satisfactory film-forming properties.

Furthermore, it has been observed that the composite pigments of the invention are stable in aqueous dispersion. On account of their constitution and their very small particle size, they also have the advantage of having a larger apparent volume fraction of the dye formed in situ by oxidation of the melanin pigment precursor. This property has the consequence of allowing smaller amounts of melanin pigment precursor to be introduced into the composite particles of the invention in order to obtain the same coloring effect.

The composite melanin pigments of the invention have a wide range of shades and can be used in many types of make-up products.

The composite melanin pigments of the invention also have a coefficient of absorption of ultraviolet radiation which renders them satisfactory for use in products for protecting the human epidermis against the effects of UV radiation.

Moreover, the composite melanin pigments of the invention act effectively against oxygen-containing free radicals, in particular against the extremely harmful hydroxyl free radicals (°OH) and make it possible in particular to combat ageing of the skin and to protect the skin and the exoskeleton against the effects of free radicals induced, for example, by atmospheric pollutants and/or by ultraviolet radiation.

Hereinbelow, the term "exoskeleton" will refer to: head hair, other hairs such as the eyelashes and the eyebrows, or the nails.

The invention thus relates to composite melanin pigments in the form of particles comprising a spherical core less than 1 µm in diameter, comprising at least one wax and at least one emulsifying surfactant, and an outer layer which envelops the core, comprising at least one compound resulting from the oxidative polymerization of a melanin pigment precursor.

The wet particles are preferably less than 500 nm in size. They generally include wax or a mixture of waxes whose melting point ranges from 50 to 100° C. They also contain one or more emulsifying surfactants and optionally one or more oily or pasty fatty additives and/or one or more liposoluble active agents which will be specified later.

The wax or the mixture of waxes contained in the core of the composite pigment particles of the invention generally represents from 20 to 97% by weight, and more preferably from 40 to 85%, of the total weight of the core.

The waxes or the wax mixtures used are preferably selected from carnauba wax, candelilla wax, alfalfa wax and mixtures thereof.

In addition to the waxes or the wax mixtures mentioned above, it is also possible to use:

paraffin wax;

ozokerite;

plant waxes such as olive wax, rice wax, hydrogenated jojoba wax, absolute waxes from flowers such as essential wax of blackcurrant flower;

animal waxes such as beeswaxes, modified beeswaxes (cerabellina);

marine waxes such as those sold under the name M82 by Sophim;

natural or synthetic ceramides;

polyethylene waxes.

The core of the composite pigment particles preferably contain at least 20% by weight, and more preferably at least 50% by weight, of wax selected from carnauba wax, candelilla wax, alfalfa wax and mixtures thereof relative to the total amount of wax present in the core.

In addition to the waxes or the wax mixtures mentioned above, it is also possible to use one or more oily or pasty fatty additives such as, for example:

plant oils such as sunflower oil, jojoba oil, etc., mineral oils such as liquid paraffin, fluid silicone oils, fluoro oils and waxes, petroleum jelly, lanolin.

The additional fatty additives and/or oils in the core of the composite pigment particles of the invention can represent up to 30% by weight of the total weight of the core.

In addition to the waxes or the wax mixtures mentioned above, it is also possible to use one or more liposoluble active agents such as liposoluble UV screening agents and liposoluble vitamins. They can represent up to 30% by weight, and more preferably up to 10% by weight, of the total weight of the core.

The emulsifying surfactant(s) present in the waxy core of the composite pigment particles of the invention are selected from anionic, cationic and nonionic surfactants and mixtures thereof, usually used in the preparation of wax microdispersions, in particular the surfactants used in the microdispersions described in European patent application EP-A-0,557,196 (U.S. Pat. No. 5,849,278), the disclosure of which is specifically incorporated by reference herein. They are present in concentrations preferably ranging from 3 to 50% by weight and more particularly from 10 to 30% by weight relative to the total weight of the waxy core. The wax(es)/surfactant(s) weight ratio preferably ranges from 1 to 30 and more particularly from 2 to 10.

According to a particularly preferred form of the invention, the core of the composite pigment particles of the invention also contains a nonionic, amphiphilic compound with a long polar head as an agent for stabilizing the wax particles constituting the core of the composite pigments.

The reason for this is that the inventors observed that aqueous dispersions of composite pigments and of wax particles as defined above, in the presence of certain additives such as salts, preserving agents or fragrances, can become destabilized on account of a phenomenon of flocculation of the wax particles and of the pigment particles constituting their core. The inventors have discovered, surprisingly, that the use of nonionic amphiphilic molecules with a long polar head make it possible to overcome these problems of flocculation of the wax particles and of the pigment particles in aqueous suspension.

The stabilizing nonionic amphiphilic molecules of the invention generally have, on the one hand, a hydrocarbon chain which can be linear or branched, saturated or unsaturated, aliphatic or aromatic, and, on the other hand, contain at least 50 polar or hydrophilic units constituting the polar head. These polar units can be, for example, ethylene oxide, propylene oxide, glycerol or acrylamide units.

They are selected in particular from polyalkoxylated and/or polyglycerolated fatty acids or amides, polyalkoxylated and/or polyglycerolated fatty acid esters of polyols, polyalkoxylated and/or polyglycerolated alkylphenols or fatty alcohols, polyalkoxylated and/or polyglycerolated 1,2- or 1,3-alkanediols or -alkenediols, dodecyl thioethers of polyacrylamide, alkoxylated derivatives of fatty acids or of fatty alcohols of lanolin containing at least 50 polar or hydrophilic units constituting the polar head.

The nonionic amphiphilic compounds have a long polar head of the following formula:

$$RO-(CH_2CH_2O)n-H \quad (I)$$

in which:

R denotes an alkyl, alkenyl or aryl radical containing at least 8 carbon atoms and n is a number ranging from 70 to 200 and more particularly from 100 to 200. These molecules are described and prepared in Japanese patent application JP-A-61065811, the disclosure of which is specifically incorporated by reference herein.

The nonionic amphiphilic compounds with a long polar head are present in concentrations preferably ranging from 1 to 40% by weight and more particularly from 5 to 20% by weight relative to the total weight of the waxy core. The emulsifying surfactant(s)/nonionic amphiphilic compound (s) weight ratio preferably ranges from 1 to 50 and more particularly from 1 to 20.

The melanin pigment precursors which are used in accordance with the invention and which will lead, by oxidative polymerization, to the in situ formation of a synthetic pigment around the wax microparticles are preferably selected from:

(i) indoline compounds of the following formula (II), and the acid-addition salts thereof:

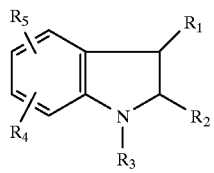

(II)

in which:

$R_1$ and $R_3$ represent, independently of each other, a hydrogen atom or a $C_1$–$C_4$ alkyl group;

$R_2$ denotes a hydrogen atom, a $C_1$–$C_4$ alkyl group, a carboxyl group or a $(C_1$–$C_4)$alkoxycarbonyl group;

$R_4$ denotes a hydrogen atom, a $C_1$–$C_4$ alkyl group, a hydroxyl group, a $(C_1$–$C_4)$ alkoxyamino group, a $(C_1$–$C_{10})$ alkylamino group or a halogen atom;

$R_5$ denotes a hydrogen atom, a $C_1$–$C_4$ alkyl group, a hydroxyl group, a $C_1$–$C_4$ alkoxy group or an amino group; wherein at least one of the radicals $R_4$ or $R_5$ denotes a hydroxyl, alkoxy or amino group; with the proviso that when $R_5$ denotes amino then $R_4$ is other than an alkylamino radical; or $R_4$ and $R_5$ form an alkylenedioxy ring and are in position 5 and 6;

(ii) indole compounds of the following formula (III), and the acid-addition salts thereof:

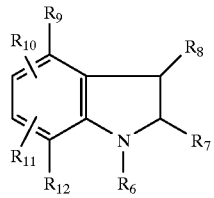

(III)

in which:

$R_6$ and $R_8$ represent, independently of each other, a hydrogen atom or a $C_1$–$C_4$ alkyl group;

$R_7$ denotes a hydrogen atom, a $C_1$–$C_4$ alkyl group, a carboxyl group or a $(C_1$–$C_4)$alkoxycarbonyl group;

$R_9$ and $R_{12}$ denote, independently of each other, a hydrogen atom, a $C_1$–$C_4$ alkyl group, a hydroxyl group, a $C_1$–$C_4$ alkoxy group, an amino group, a $(C_2$–$C_4)$ acyloxy group or a $(C_2$–$C_4)$acylamino group;

$R_{10}$ denotes a hydrogen atom, a $C_1$–$C_4$ alkyl group, a hydroxyl group, a $C_1$–$C_4$ alkoxy group, an amino group, a $(C_2$–$C_4)$acyloxy group, a $(C_2$–$C_4)$acylamino group, a halogen atom or a trimethylsilyloxy group;

$R_{11}$ denotes a hydrogen atom, a hydroxyl group, a $C_1$–$C_4$ alkoxy group, an amino group, a $(C_2$–$C_4)$acyloxy group, a $(C_2$–$C_4)$acylamino group, a hydroxy$(C_2$–$C_4)$ alkylamino group or a trimethylsilyloxy group;

$R_{10}$ and $R_{11}$ may form, together with the carbon atoms to which they are attached, a methylenedioxy ring optionally substituted with a $C_1$–$C_4$ alkyl, a $C_1$–$C_4$ alkoxy or a carbonyldioxy ring;

at least one of the groups $R_9$ to $R_{12}$ represents a group OZ or NHR and only one of the groups denotes NHR;

not more than two of the groups $R_9$ to $R_{12}$ represent a group OZ, when Z denotes hydrogen, and are in position 5 and 6;

at least one of the groups $R_9$ to $R_{12}$ denotes hydrogen, in the case where only one of these groups denotes hydrogen, only one of the groups denotes a group NHR or OZ and the others denote a $C_1$–$C_4$ alkyl group;

R denotes a hydrogen atom, a $C_2$–$C_4$ acyl group or a $C_2$–$C_4$ hydroxyalkyl group;

Z denotes a hydrogen atom, a $C_2$–$C_4$ acyl group, a $C_1$–$C_4$ alkyl group or a trimethylsilyl group, and (iii) mixtures thereof.

The salts of the indole or indoline compounds of formula (II) or (III) mentioned above are cosmetically acceptable salts selected, for example, from hydrochlorides, hydrobromides, sulphates and methanesulphonates.

The compounds of formula (II) and the corresponding salts thereof are described in French patent application FR 2,686,248 (U.S. Pat. No. 5,496,543) and the compounds of formula (III) and the corresponding salts thereof are described in French patent application FR 2,686,345 (U.S. Pat. No. 5,449,403), the disclosures of which are specifically incorporated by reference herein.

Among the compounds of formula (II) and the salts thereof, mention may be made more particularly of 5,6-dihydroxyindoline and the acid-addition salts thereof, such as hydrobromides.

Among the compounds of formula (III) and the salts thereof, mention may be made more particularly of 6-hydroxyindole, 5,6-dihydroxyindole and N-methyl-5,6-dihydroxyindole and the acid-addition salts thereof.

The melanin pigment precursor(s) is or are preferably used in amounts such that the weight ratio of the wax(es)/pigment formed in situ after oxidation of the melanin pigment precursor is greater than or equal to 3.

The size of the spherical particles of composite melanin pigment according to the invention is preferably less than 1 $\mu$m, more preferably less than or equal to 500 nm and still more preferably ranges from 20 to 500 nm.

Another subject of the present invention is a process for the preparation of the composite melanin pigments as defined above.

This process involves preferably dispersing and solubilizing, preferably at room temperature, preferably with gentle stirring and under an inert atmosphere, a melanin precursor as indicated above in an aqueous dispersion of spherical wax particles preferably less than 1 $\mu$m in size containing, in addition to the wax, at least one emulsifying surfactant, such as those defined above, and then oxidizing the precursor so as to polymerize it and form an outer layer which envelops each wax particle.

The polymerization step is generally carried out below the melting point of the wax or of the wax mixture constituting the wax particles, and preferably at room temperature, in order to avoid melting of the wax particles.

It can be performed in aqueous media by autoxidation in air brought about by vigorous stirring of the wax microdispersion adjusted to a neutral or alkaline pH.

According to another type of process, the products in accordance with the invention can be prepared in the presence of an oxidizing agent such as hydrogen peroxide, peracids and persalts.

Among the peracids and persalts, mention may be made of periodic acid and its water-soluble salts, permanganates and dichromates, such as sodium or potassium permanganate or dichromate, ammonium persulphate and organic peracids. The preferred periodic acid salt is sodium periodate.

Other oxidizing agents may be selected from alkaline chlorites, silver oxide, ferric chloride, lead oxide, sodium nitrite; rare-earth metal salts such as, in particular, cerium salts.

Organic oxidizing agents may be selected from ortho- and para-benzoquinones, ortho- and para-benzoquinone monoimines and diimines, 1,2- and 1,4-naphthoquinones and 1,2- and 1,4-naphthoquinone mono- or diimines.

Lastly, the oxidation can be carried out using iodide such as an alkali metal, alkaline-earth metal or ammonium iodide in the presence of hydrogen peroxide.

These oxidizing agents can optionally be activated by a pH modifier. The pH modifiers are acidifying or basifying agents usually used in cosmetics.

It is also possible to perform the process by enzymatic oxidation. This oxidation is carried out in an oxidizing medium and in the presence of an enzyme with oxidizing or peroxidizing activity, such as enzymes selected from horse-radish peroxidase, chloroperoxidase, milk peroxidase, cytochrome C-peroxidase and products having similar activity, those of peroxidizing enzymes such as hemoglobin, methemoglobin, myoglobin and metmyoglobin.

Hydrogen peroxide, periodic acid and its salts, potassium permanganate, sodium hypochlorite, ammonium persulphate, sodium nitrite and the iodide/hydrogen peroxide system are preferably used as oxidizing agents. When an iodide is used in the presence of aqueous hydrogen peroxide solution, it is preferably sodium or potassium iodide in a weight concentration ranging from 1 to 6% relative to the weight of the reaction medium.

According to a preferred embodiment of the process of the invention, a nonionic, amphiphilic compound with a long polar head, such as those mentioned above, is incorporated under hot or cold conditions into the wax microdispersion before dispersing the melanin pigment precursor therein. This amphiphilic compound makes it possible to stabilize the wax microdispersion and to avoid the flocculation problems mentioned above.

After the polymerization, an aqueous dispersion of composite pigment particles in accordance with the present invention are obtained, this dispersion being opaque, fluid and stable over time and its color varies, depending on the choice of the melanin precursor, over a wide range of shades.

This composition can be dehydrated by lyophilization or spraying techniques so as to obtain the composite pigment particles in pulverulent form while at the same time retaining the particle size that they had in suspension.

Another subject of the invention includes a cosmetic or dermatological composition comprising at least one composite melanin pigment in the form of spherical particles in powder form or in the form of an aqueous dispersion, as defined above.

In their cosmetic or dermatological application, the composite melanin pigments in accordance with the invention are used in powder form or in the form of an aqueous dispersion in cosmetic compositions, in a concentration preferably ranging from 0.1 to 35% by weight, and in particular from 0.5 to 20% by weight, relative to the total weight of the composition.

They can be used in, and for the preparation of, make-up products, in particular for the eyelashes, the eyebrows, the skin or the nails, such as in the form of eyeshadows, blushers, foundations, eyeliners, mascaras for the eyelashes and the eyebrows, and nail varnishes.

They can also be used in, and for the preparation of, hair dye compositions, in particular for temporarily dyeing or making up the hair.

They can be used in, and for the preparation of, compositions for temporarily dyeing or protecting the human epidermis and/or the exoskeleton against the harmful effects of UV rays, in particular so-called antisun products.

They can be used in, and for the preparation of, compositions for protecting the skin and/or the exoskeleton against the effects of free radicals induced, for example, by atmospheric pollutants and/or by ultraviolet radiation.

When the cosmetic or dermatological compositions are make-up products for the skin, the eyelashes and the eyebrows, they can in particular be in solid or pasty form, such as oil-in-water or water-in-oil emulsions or alternatively suspensions. The compositions can also be in particular in the form of a gel, a cream, a milk, a powder, a stick or an aerosol foam.

When the cosmetic or dermatological compositions are used to protect the human epidermis and/or the exoskeleton against UV radiation, they can be in the form of suspensions or dispersions or alternatively in the form of emulsions such as creams and milks, ointments, gels, solid sticks or aerosol foams. When they are used in the form of emulsions, they can also contain surfactants that are well known in the state of the art, such as anionic, nonionic, cationic or amphoteric surfactants.

The cosmetic or dermatological compositions of the invention can also contain fatty substances, organic solvents, silicones, thickeners, softeners, sunscreens, antifoaming agents, moisturizers, fragrances, preserving agents, antioxidants, fillers, sequestering agents, treatment agents such as anionic, cationic, nonionic or amphoteric polymers or mixtures thereof, propellants, and acidifying or basifying agents.

The cosmetic or dermatological compositions in accordance with the invention can also contain, in addition to the composite melanin pigments as defined above, pigments generally used in cosmetics, in particular nacreous and/or pearlescerit pigments which make it possible to vary the colorations which can be obtained, or to increase the protection against ultraviolet radiation. In the latter case, pigments or nanopigments of metal oxides such as titanium oxide, zinc oxide, cerium oxide or zirconium oxide are used more particularly. The nanopigments which are preferably used are pigments having an average diameter of less than 100 nm and preferably ranging from 5 to 50 nm. They may be coated or non-coated.

The coated pigments are pigments which have undergone one or more surface treatments of a chemical, electronic, mechanochemical and/or mechanical nature with compounds as described, for example, in *Cosmetics and Toiletries*, February 1990, Vol. 105, pages 53–64 (the disclosure of which is incorporated by reference herein), such as amino acids, beeswax, fatty acids, fatty alcohols, anionic surfactants, lecithins, sodium, potassium, zinc, iron or aluminum salts of fatty acids, metal (titanium or aluminum) alkoxides, polyethylene, silicones, proteins (collagen, elastin), alkanolamines, silicon oxides, metal oxides or sodium hexametaphosphate.

When the cosmetic compositions of the invention are used for treating the nails, the composite melanin pigment of the invention is introduced into a nail varnish medium comprising a volatile solvent and polymers.

These products can be applied directly in powder form or by means of cosmetic compositions as defined above.

The examples which follow are intended to illustrate the invention without, however, being limiting in nature.

Examples of the Preparation of Microdispersions of Composite Melanin Pigments

EXAMPLE A

| | |
|---|---|
| Carnauba wax | 10% by weight |
| Polyoxyethylenated (25 EO) fatty alcohol mixture and lanolin alcohol sold under the name SOLULAN 25 by the company Amerchol (emulsifying surfactant) | 2.5% by weight |
| Polyoxyethylenated stearyl alcohol sold under the name BRIJ 700 by the company ICI (stabilizer) | 2% by weight |
| Product resulting from the oxidation of 5,6-dihydroxyindole | 1% by weight |
| 0.5 M $KH_2PO_4/K_2HPO_4$ buffer pH7 | 10% by weight |
| Water | 74.5% by weight |

Step 1: Preparation of the Wax Microdispersion

The following ingredients were introduced into a wide-necked 250 $cm^3$ soda-lime glass flask:

| | |
|---|---|
| carnauba wax | 17.235 g |
| SOLULAN 25 (emulsifying surfactant) | 4.305 g |

The wax and the emulsifying surfactant were brought to 90° C. while homogenizing with moderate stirring. 128.46 g of water, also brought to 90° C., was incorporated while the stirring continued.

The microemulsion obtained was cooled to room temperature and formed a microdispersion of wax-based grains.

Average diameter of the wax particles: 112 nm

Size polydispersity of the particles: 0.06 (measured by quasi-elastic light scattering, using a machine of the type Amtec/BI 2030 AT)

Step 2: Stabilization of the Wax Microdispersion 2.475 g of stabilizer (BRIJ 700) were introduced into a wide-necked 125 $cm^3$ soda-lime glass flask and the mass was made up to 110 g with the cooled, wax microdispersion obtained in step 1. The stabilizer was dissolved in the dispersion with magnetic stirring.

The wax microdispersion obtained had the following granulometry:

Average diameter of the wax particles: 119 nm

Size polydispersity of the particles: 0.07 (measured by quasi-elastic light scattering, using a machine of the type Amtec/BI 2030 AT)

Step 3: Preparation of the Microdispersion of Composite Melanin Pigment Solubilization of the Melanin Precursor in the Wax Microdispersion 1.11 g of 5,6-dihydroxyindole was introduced into a wide-necked 125 $cm^3$ soda-lime glass flask and the mass was then made up to 100 g with the microdispersion obtained in step 2.

Nitrogen was introduced into the flask above the mixture obtained, along with a magnetic bar, and the flask was immediately sealed. The 5,6-dihydroxyindole was dissolved with magnetic stirring for 2 hours.

In Situ Polymerization of the Melanin Precursor in the Wax Microdispersion 10 g of 0.5 M $KH_2PO_4/K_2HPO_4$ buffer solution of pH7 were introduced into another wide-necked 125 $cm^3$ soda-lime glass flask and the mass was then made up to 100 g with the wax microdispersion containing the 5,6-dihydroxyindole. A magnetic bar was introduced and the flask was then sealed with a perforated cap. The mixture was left to act with magnetic stirring for 48 hours until polymerization of the 5,6-dihydroxyindole ended.

A dispersion of composite pigment particles of liquid, brown-black, opaque appearance was obtained, having the following granulometry:

Average diameter of the wax particles: 122 nm

Size polydispersity of the particles: 0.08 (measured by quasi-elastic light scattering using a machine of the type Amtec/BI 2030 AT)

EXAMPLE B

| Carnauba wax | 9% by weight |
| N-Oleoyldihydrosphingosine (ceramide) | 1% by weight |
| SOLULAN 25 (emulsifying surfactant) | 2.5% by weight |
| BRIJ 700 (stabilizer) | 2% by weight |
| Product resulting from the oxidation of 5,6-dihydroxyindole | 1% by weight |
| 0.5 M $KH_2PO_4/K_2HPO_4$ buffer pH7 | 10% by weight |
| Water | 74.5% by weight |

The process was performed under the same conditions as in steps 1 to 3 of the preparation process of Example A, with the following ingredients:

| carnauba wax | 15.510 g |
| N-Oleoyldihydrosphingosine (ceramide) | 1.725 g |
| SOLULAN 25 (emulsifying surfactant) | 4.305 g |

The N-oleoyidihydrosphingosine was used with the wax under the same conditions indicated in step 1 of the process of Example A.

The wax microdispersion obtained in step 1 had the following granulometry: average diameter of the wax particles: 108 nm size polydispersity of the particles: 0.09 (measured by quasi-elastic light scattering using a machine of the type Amtec/BI 2030 AT)

The wax microdispersion obtained in step 2 had the following granulometry:

average diameter of the wax particles: 116 nm size polydispersity of the particles: 0.1 (measured by quasi-elastic light scattering using a machine of the type Amtec/BI 2030 AT)

In step 3, a dispersion of particles of composite melanin pigment of liquid, brown-black, opaque appearance was obtained, having the following granulometry: average diameter of the wax particles: 124 nm size polydispersity of the particles: 0.09 (measured by quasi-elastic light scattering using a machine of the type Amtec/BI 2030 AT)

EXAMPLE C

| Carnauba wax | 9% by weight |
| 1-(2'-F-Hexylethylthio)-3-(2"-ethylhexyloxy)-2-propanol (fluoro oil) | 1% by weight |
| SOLULAN 25 (emulsifying surfactant) | 2.5% by weight |
| BRIJ 700 (stabilizer) | 2% by weight |
| Product resulting from the oxidation of 5,6-dihydroxyindole | 1% by weight |
| 0.5 M $KH_2PO_4/K_2HPO_4$ buffer pH7 | 10% by weight |
| Water | 74.5% by weight |

The process was performed under the same conditions as in steps 1 to 3 of the preparation process of Example A, with the following ingredients:

| carnauba wax | 15.510 g |
| 1-(2'-F-hexylethylthio)-3-(2"-ethylhexyloxy)-2-propanol (fluoro oil) | 1.725 g |
| SOLULAN 25 (emulsifying surfactant) | 4.305 g |

The fluoro oil was used with the wax under the same conditions indicated in step 1 of the process of Example A.

The wax microdispersion obtained in step 1 had the following granulometry:

average diameter of the wax particles: 108 nm size polydispersity of the particles: 0.07 (measured by quasi-elastic light scattering using a machine of the type Amtec/BI 2030 AT)

The wax microdispersion obtained in step 2 had the following granulometry:

average diameter of the wax particles: 114 nm size polydispersity of the particles: 0.07 (measured by quasi-elastic light scattering using a machine of the type Amtec/BI 2030 AT)

In step 3, a dispersion of particles of composite melanin pigment of liquid, brown-black, opaque appearance was obtained, having the following granulometry:

average diameter of the wax particles: 116 nm size polydispersity of the particles: 0.08 (measured by quasi-elastic light scattering using a machine of the type Amtec/BI 2030 AT)

EXAMPLE D

| Carnauba wax | 20% by weight |
| Oxyethylenated glyceryl monostearate (30 EO) sold under the name "TAGAT S" by the company Goldschmidt (emulsifier) | 5.0% by weight |
| BRIJ 700 (stabilizer) | 2% by weight |
| Preserving agent | 0.2% by weight |
| Product resulting from the oxidation of 5,6-dihydroxyindole | 1% by weight |
| 0.5 M $KH_2PO_4/K_2HPO_4$ buffer pH8 | 10% by weight |
| Water | 61.8% by weight |

Step 1: Preparation of the Wax Microdispersion

The following ingredients were introduced into a wide-necked 250 cm³ soda-lime glass flask:

| carnauba wax | 48.279 g |
| TAGAT S (emulsifying surfactant) | 12.054 g |

The wax and the emulsifier were brought to 90° C. while homogenizing with moderate stirring. 149.667 g of a solution containing water and the preserving agent, also brought to 90° C., were incorporated while the stirring continued.

The microemulsion obtained was cooled to room temperature and formed a microdispersion of wax-based grains.

Average diameter of the wax particles: 201 nm

Size polydispersity of the particles: 0.1 (measured by quasi-elastic light scattering, using a machine of the type Amtec/BI 2030 AT)

Step 2: Stabilization of the Wax Microdispersion 8.736 g of stabilizer (BRIJ 700) were introduced into a wide-necked 500 cm³ soda-lime glass flask and the mass was made up to 390 g with the cooled wax microdispersion obtained in step 1. The stabilizer was dissolved in the dispersion with magnetic stirring.

The wax microdispersion obtained had the following granulometry:

Average diameter of the wax particles: 204 nm

Size polydispersity of the particles: 0.1 (measured by quasi-elastic light scattering, using a machine of the type Amtec/BI 2030 AT)

Step 3: Preparation of the Microdispersion of Composite Melanin Pigment Solubilization of the Melanin Precursor in the Wax Microdispersion 4.273 g of 5,6-dihydroxyindole were introduced into a wide-necked 500 cm³ soda-lime glass flask and the mass was then made up to 385 g with the microdispersion obtained in step 2.

Nitrogen was introduced into the flask above the mixture obtained, along with a magnetic bar, and the flask was immediately sealed. The 5,6-dihydroxyindole was dissolved with magnetic stirring for 2 hours.

In Situ Polymerization of the Melanin Precursor in the Wax Microdispersion 42 g of 0.5 M $KH_2PO_4/K_2HPO_4$ buffer solution of pH 8 were introduced into another wide-necked 500 cm³ soda-lime glass flask and the mass was then made up to 420 g with the wax microdispersion containing the 5,6-dihydroxyindole. A magnetic bar was introduced and the flask was then sealed with a perforated cap. The mixture was left to act with magnetic stirring for 72 hours until polymerization of the 5,6-dihydroxyindole ended.

A dispersion of composite pigment particles of liquid, black, opaque appearance was obtained, having the following granulometry:

Average diameter of the wax particles: 206 nm

Size polydispersity of the particles: 0.08 (measured by quasi-elastic light scattering using a machine of the type Amtec/BI 2030 AT)

EXAMPLE E

| | |
|---|---|
| Carnauba wax | 10% by weight |
| SOLULAN 25 (emulsifying surfactant) | 2.5% by weight |
| BRIJ 700 (stabilizer) | 2% by weight |
| Product resulting from the oxidation of 6-monohydroxyindole | 1% by weight |
| 0.5 M $KH_2PO_4/K_2HPO_4$ buffer pH7 | 10% by weight |
| Water | 74.5% by weight |

The process was performed under the same conditions as in steps 1 to 3 of the preparation process of Example A. A dispersion of particles of composite melanin pigment of liquid, rust-crimson, opaque appearance was obtained, having the following granulometry:

average diameter of the wax particles: 115 nm size polydispersity of the particles: 0.11 (measured by quasi-elastic light scattering using a machine of the type Amtec/BI 2030 AT)

EXAMPLE F

| | |
|---|---|
| Carnauba wax | 10% by weight |
| SOLULAN 25 (emulsifying surfactant) | 2.5% by weight |
| BRIJ 700 (stabilizer) | 2% by weight |
| Product resulting from the oxidation of N-methyl-5,6-dihydroxyindole | 1% by weight |
| 0.5 M $KH_2PO_4/K_2HPO_4$ buffer pH7 | 10% by weight |
| Water | 74.5% by weight |

The process was performed under the same conditions as in steps 1 to 3 of the preparation process of Example A. A dispersion of particles of composite melanin pigment of liquid, dark green, opaque appearance was obtained, having the following granulometry:

average diameter of the wax particles: 105 nm size polydispersity of the particles: 0.08 (measured by quasi-elastic light scattering using a machine of the type Amtec/BI 2030 AT)

EXAMPLE G

| | |
|---|---|
| Carnauba wax | 10% by weight |
| SOLULAN 25 (emulsifying surfactant) | 2.5% by weight |
| BRIJ 700 (stabilizer) | 2% by weight |
| Product resulting from the oxidation of 5,6-dihydroxyindoline hydrobromide | 1% by weight |
| 0.5 M $KH_2PO_4/K_2HPO_4$ buffer pH7 | 10% by weight |
| Water | 74.5% by weight |

The process was performed under the same conditions as in steps 1 to 3 of the preparation process of Example A. A dispersion of particles of composite melanin pigment of liquid, black with reddish tinges, opaque appearance was obtained, having the following granulometry:

average diameter of the wax particles: 104 nm size polydispersity of the particles: 0.06 (measured by quasi-elastic light scattering using a machine of the type Amtec/BI 2030 AT)

EXAMPLE H

| | |
|---|---|
| Carnauba wax | 5% by weight |
| Polyoxyethylenated cetyl alcohol (20 EO) sold under the name BRIJ 58 by the company ICI (emulsifying surfactant) | 2.34% by weight |
| BRIJ 700 (stabilizer) | 1% by weight |
| Product resulting from the oxidation of 5,6-dihydroxyindole | 0.5% by weight |
| Water | 91.16% by weight |

Step 1: Preparation of the Wax Microdispersion

The following ingredients were introduced into a wide-necked 250 cm³ soda-lime glass flask:

| | |
|---|---|
| carnauba wax | 7.5 g |
| BRIJ 58 (emulsifying surfactant) | 3.51 g |
| BRIJ 700 (stabilizer) | 1.5 g |

The wax, the emulsifier and the stabilizer were brought to 90° C. while homogenizing with moderate stirring. 134.39 g of water, also brought to 90° C., were incorporated while the stirring continued.

The microemulsion obtained was cooled to room temperature and formed a microdispersion of wax-based grains. The wax microdispersion obtained had the following granulometry:

Average diameter of the wax particles: 50.7 nm

Size polydispersity of the particles: 0.17 (measured by quasi-elastic light scattering, using a machine of the type Amtec/BI 2030 AT)

Step 2: Preparation of the Microdispersion of Composite Melanin Pigment Solubilization of the Melanin Precursor in the Wax Microdispersion The operating conditions were identical to those for the solubilization of the melanin pigment precursor in the wax microdispersion used in the process of Example A or D.

In Situ Polymerization of the Melanin Precursor in the Wax Microdispersion

The polymerization by oxidation of 5,6-dihydroxyindole was carried out with the oxidizing system consisting of:

hydrogen peroxide ($H_2O_2$) in a proportion of 5 ml of 20-volumes $H_2O_2$ per gram of 5,6-dihydroxyindole, and potassium iodide (KI) in a proportion of 0.4 g per gram of 5,6-dihydroxyindole.

The mixture was left to act with magnetic stirring for 22 hours until polymerization of the 5,6-dihydroxyindole ended.

A dispersion of composite pigment particles of liquid, black, opaque appearance was obtained, having the following granulometry:

average diameter of the wax particles: 54 nm size polydispersity of the particles: 0.19 (measured by quasi-elastic light scattering, using a machine of the type Amtec/BI 2030 AT)

Test of Inhibition of the Production of Ethylene by the Formulation of Example H The following ingredients were introduced, in the following order, into a Petri dish 32 mm in diameter:

1.4 ml of 50 mM phosphate buffer (pH=7.4),

100 µl of 200 mM methionine solution,

100 µl of 4 mM ferric chloride solution,

100 µl of the test product,

100 µl of 4 mM EDTA (ethylenediamine tetraacetic acid) solution,

100 µl of 400 mM NADH (nicotinamide adenine dinucleotide, reduced form) solution, 100 µl of 2 mM riboflavine solution.

The sample had a total volume of 2 ml.

This dish was then placed on an aluminum dish and covered with a quartz cell in order to be exposed to UVA rays (365 nm) at a dose of 1 J/cm$^2$. When exposed to UVA rays, the mixture composed of NADH, riboflavine, ferric chloride and EDTA generates reduced oxygen species: $O_2^{o-}$, $H_2O_2$ and mainly the hydroxyl radical $^oOH$. The latter reacted with methionine to release ethylene, the amount of which was measured by gas chromatography.

The larger the amount of free radicals formed, the larger the amount of ethylene released. The results are expressed as a percentage of inhibitory power, corresponding to the percentage decrease in the production of ethylene relative to the control (containing 100 µl of phosphate buffer replacing the test product).

The composition of Example H allowed the production of ethylene to be reduced by 90% and thus had good inhibitory power on the formation of $^oOH$ radicals.

Examples of Cosmetic Formulations

EXAMPLE 1

Mascara
The following composition is prepared:

| | |
|---|---|
| Microdispersion of composite pigment according to Example D | 89.5 g |
| Hydroxyethylcellulose sold under the name "CELLOSIZE QP 4400M" by the company Amerchol | 1 g |
| Gum arabic | 1.5 g |
| Panthenol | 1.0 g |
| NaOH pH7 | qs |
| Water | 7.0 g |

Procedure

The process was performed by dilution of the microdispersion according to Example D in two steps. The polymer (s) present in the formulation was/were incorporated, at room temperature, into the microdispersion according to Example D with stirring, optionally with the addition of water, if necessary, in order to obtain a homogeneous preparation. The pigments were then dispersed. The formulation can be ground.

This composition was applied to the eyelashes. When applied, it was observed that the eyelashes were shiny and have a good curvature and good flexibility.

EXAMPLE 2

Mascara

| | |
|---|---|
| Microdispersion of composite pigment according to Example D | 86 g |
| Glycerol | 3 g |
| Polyvinylpyrrolidone sold under the name "LUVISKOL K90" by the company BASF | 4 g |
| Sodium polymethacrylate | 1 g |
| NaOH pH7 | qs |
| Water | 7.0 g |

This formulation was prepared under the same conditions as in Example 1. This composition was applied to the eyelashes. When applied, it was observed that the eyelashes were shiny and have good curvature and good flexibility.

EXAMPLE 3

Suncream
Fatty phase 1

| | |
|---|---|
| PEG-100 stearate/glyceryl stearate sold under the name ARLACEL 165 by ICI | 3 g |
| Stearic acid sold under the name STEARINE TP by Stearinerie Dubois | 1 g |
| Octyldodecanol sold under the name EUTANOL G by Henkel | 5 g |
| Cyclomethicone sold under the name DC 244 Fluid by Dow Corning | 7 g |

Aqueous phase 2 (gel)

| | |
|---|---|
| Poly(acrylic acid) sold under the name CARBOPOL 940 by Goodrich | 0.25 g |
| Triethanolamine | 1.3 g |

-continued

| Propylene glycol | 2.5 g |
| Preserving agents | qs |
| Demineralized water qs | 100 g |

Phase 3

| Microdispersion of composite pigment according to one of Examples A, B, C, E, F and G | 1 g |

Procedure

The fatty phase 1 is prepared by simple weighing and mixing of the abovementioned ingredients. The aqueous phase 2 (gel) is prepared by dispersing the Carbopol 940 in the water/propylene glycol mixture which has been preheated to 80° C., with stirring using a Moritz-type mixer until completely homogeneous, after which the mixture is neutralized to pH 6–7 with triethanolamine. A gel is thus obtained. The fatty phase is heated to 80° C. and the aqueous gel obtained is added, after which the mixture is stirred using the Moritz-type mixer. The mixture is allowed to cool to about 45° C. and the preserving agents are added and dispersed with stirring using the Moritz-type mixer. Lastly, the wax microdispersion (phase 3) is introduced at room temperature and dispersed in the mixture, with stirring, until completely homogeneous.

We claim:

1. A composite melanin pigment in the form of particles, wherein said particles comprise a spherical core less than 1 μm in diameter and an outer layer which envelops said spherical core, and further wherein said spherical core comprises at least one wax and at least one emulsifying surfactant, and said outer layer comprises at least one compound resulting from the oxidative polymerization of a melanin pigment precursor.

2. A composite melanin pigment according to claim 1, wherein said at least one wax is present in a concentration ranging from 20 to 97% by weight, relative to the total weight of the core.

3. A composite melanin pigment according to claim 2, wherein said at least one wax is present in a concentration ranging from 40 to 85% by weight, relative to the total weight of the core.

4. A composite melanin pigment according to claim 1, wherein said at least one wax has a melting point ranging from 50 to 100° C.

5. A composite melanin pigment according to claim 1, wherein said at least one wax is selected from carnauba wax, candelilla wax, and alfalfa wax.

6. A composite melanin pigment according to claim 5, wherein said at least one wax selected from carnauba wax, candelilla wax, and alfalfa wax is present in a concentration of at least 20% by weight, relative to the total amount of wax present in said spherical core.

7. A composite melanin pigment according to claim 6, wherein said at least one wax selected from carnauba wax, candelilla wax, and alfalfa wax is present in a concentration of at least 50% by weight, relative to the total amount of wax present in said spherical core.

8. A composite melanin pigment according to claim 5, wherein said spherical core further comprises at least one wax selected from:
  paraffin wax;
  ozokerite;
  plant waxes;
  animal waxes;
  marine waxes;
  natural and synthetic ceramides; and
  polyethylene waxes.

9. A composite melanin pigment according to claim 1, wherein said spherical core further comprises at least one oily or pasty fatty additive.

10. A composite melanin pigment according to claim 9, wherein said at least one oily or pasty fatty additive is present in a concentration of up to 30% by weight, relative to the total weight of said spherical core.

11. A composite melanin pigment according to claim 1, wherein said spherical core further comprises at least one liposoluble active agent.

12. A composite melanin pigment according to claim 1, wherein said at least one liposoluble active agent is present in a concentration of up to 30% by weight, relative to the total weight of said spherical core.

13. A composite melanin pigment according to claim 12, wherein said at least one liposoluble active agent is present in a concentration of up to 10% by weight, relative to the total weight of said spherical core.

14. A composite melanin pigment according to claim 1, wherein said at least one emulsifying surfactant is present in a concentration ranging from 3 to 50% by weight, relative to the total weight of said spherical core.

15. A composite melanin pigment according to claim 14, wherein said at least one emulsifying surfactant is present in a concentration ranging from 10 to 30% by weight, relative to the total weight of said spherical core.

16. A composite melanin pigment according to claim 1, wherein the weight ratio of said at least one wax to said at least one emulsifying surfactant ranges from 1:1 to 30:1.

17. A composite melanin pigment according to claim 16, wherein the weight ratio of said at least one wax to said at least one emulsifying surfactant ranges from 2:1 to 10:1.

18. A composite melanin pigment according to claim 1, wherein said spherical core further comprises at least one nonionic amphiphilic compound with a long polar head.

19. A composite melanin pigment according to claim 18, wherein said nonionic aniphiphilic compound with a long polar head has a linear or branched, saturated or unsaturated, aliphatic or aromatic hydrocarbon chain and wherein said long polar head comprises at least 50 polar or hydrophilic units.

20. A composite melanin pigment according to claim 18, wherein said at least one nonionic amphiphilic compound with a long polar head is selected from: polyalkoxylated and polyglycerolated fatty acids and amides, polyalkoxylated and polyglycerolated fatty acid esters of polyols, polyalkoxylated and polyglycerolated alkylphenols and fatty alcohols, polyalkoxylated and polyglycerolated 1,2- and 1,3-alkanediols and -alkenediols, dodecyl thioethers of polyacrylamide, alkoxylated derivatives of fatty acids, and fatty alcohols of lanolin, said at least one nonionic amphiphilic compound containing at least 50 polar or hydrophilic units constituting the polar head.

21. A composite melanin pigment according to claim 18, wherein said at least one nonionic amphiphilic compound with a long polar head is selected from compounds of the formula (I):

$$RO-(CH_2CH_2O)_n-H \qquad (I)$$

in which R denotes an alkyl, alkenyl or aryl radical containing at least 8 carbon atoms and n is a number ranging from 70 to 200.

22. A composite melanin pigment according to claim 21, wherein n ranges from 100 to 200.

23. A composite melanin pigment according to claim 18, wherein said at least one nonionic amphiphilic compound with a long polar head is present in a concentration ranging from 1 to 40% by weight, relative to the total weight of said spherical core and wherein the weight ratio of said at least one emulsifying surfactant to said nonionic amphiphilic compound ranges from 1:1 to 50:1.

24. A composite melanin pigment according to claim 23, wherein said weight ratio ranges from 1:1 to 20:1.

25. A composite melanin pigment according to claim 23, wherein the concentration of said at least one nonionic amphiphilic compound with a long polar head ranges from 5 to 20% by weight, relative to the total weight of said spherical core.

26. A composite melanin pigment according to claim 1, wherein said at least one melanin pigment precursor is selected from:
(i) indoline compounds of the formula (II), and the acid-addition salts thereof:

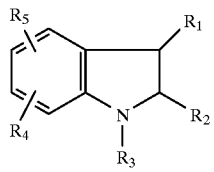

(II)

in which:
$R_1$ and $R_3$ represent, independently of each other, a hydrogen atom or a $C_1$–$C_4$ alkyl group;
$R_2$ denotes a hydrogen atom, a $C_1$–$C_4$ alkyl group, a carboxyl group or a $(C_1$–$C_4)$alkoxycarbonyl group;
$R_4$ denotes a hydrogen atom, a $C_1$–$C_4$ alkyl group, a hydroxyl group, a $(C_1$–$C_4)$ alkoxyamino group, a $(C_1$–$C_{10})$ alkylamino group or a halogen atom;
$R_5$ denotes a hydrogen atom, a $C_1$–$C_4$ alkyl group, a hydroxyl group, a $C_1$–$C_4$ alkoxy group or an amino group;
wherein at least one of the radicals $R_4$ or $R_5$ denotes a hydroxyl, alkoxy or amino group, with the proviso that when $R_5$ denotes amino, $R_4$ is other than an alkylamino radical; or
R4 and R5 form an alkylenedioxy ring and are in position 5 and 6;
(ii) indole compounds of the formula (III), and the acid-addition salts thereof:

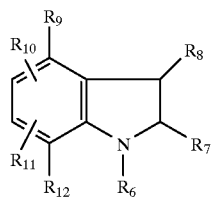

(III)

in which:
$R_6$ and $R_8$ represent, independently of each other, a hydrogen atom or a $C_1$–$C_4$ alkyl group;
$R_7$ denotes a hydrogen atom, a $C_1$–$C_4$ alkyl group, a carboxyl group or a $(C_1$–$C_4$ )alkoxycarbonyl group;

$R_9$ and $R_{12}$ denote, independently of each other, a hydrogen atom, a $C_1$–$C_4$ alkyl group, a hydroxyl group, a $C_1$–$C_4$ alkoxy group, an amino group, a $(C_2$–$C_4)$ acyloxy group or a $(C_2$–$C_4)$acylamino group;

$R_{10}$ denotes a hydrogen atom, a $C_1$–$C_4$ alkyl group, a hydroxyl group, a $C_1$–$C_4$ alkoxy group, an amino group, a $(C_2$–$C_4)$acyloxy group, a $(C_2$–$C_4)$acylamino group, a halogen atom or a trimethylsilyloxy group;

$R_{11}$ denotes a hydrogen atom, a hydroxyl group, a $C_1$–$C_4$ alkoxy group, an amino group, a $(C_2$–$C_4)$acyloxy group, a $(C_2$–$C_4)$acylamino group, a hydroxy$(C_2$ –$C_4)$ alkylamino group or a trimethylsilyloxy group;

$R_{10}$ and $R_{11}$ may form, together with the carbon atoms to which they are attached, a methylenedioxy ring optionally substituted with a $C_1$–$C_4$ alkyl, a $C_1$–$C_4$ alkoxy or a carbonyldioxy ring;

at least one of the groups $R_9$ to $R_{12}$ represents a group OZ or NHR and only one of said groups denotes NHR;

not more than two of the groups $R_9$ to $R_{12}$ represent a group OZ, when Z denotes hydrogen and when two of the groups $R_9$ to $R_{12}$ are in position 5 and 6;

at least one of the groups $R_9$ to $R_{12}$ denotes hydrogen, and when only one of these groups denotes hydrogen, only one of said groups denotes a group NHR or OZ and the others denote a $C_1$–$C_4$ alkyl group;

R denotes a hydrogen atom, a $C_2$–$C_4$ acyl group or a $C_2$–$C_4$ hydroxyalkyl group; and Z denotes a hydrogen atom, a $C_2$–$C_4$ acyl group, a $C_1$–$C_4$ alkyl group or a trimethylsilyl group.

27. A composite melanin pigment according to claim 26, wherein said at least one melanin pigment precursor is selected from 5,6-dihydroxyindoline, 6-hydroxyindole, 5,6-dihydroxyindole, N-methyl-5,6-dihydroxyindole and the acid-addition salts.

28. A composite melanin pigment according to claim 1, wherein said at least one melanin pigment precursor is present in an amount such that the weight ratio of the wax(es)/pigment formed in situ after oxidation is greater than or equal to 3:1.

29. A composite melanin pigment according to claim 1, wherein said particles comprising said pigment are less than 1 μm in size.

30. A composite melanin pigment according to claim 29, wherein said particles are less than or equal to 500 nm in size.

31. A composite melanin pigment according to claim 30, wherein said particles range from 20 to 500 nm in size.

32. A process for the preparation of a composite melanin pigment according to claim 1, said process comprising:
dispersing and solubilizing, at room temperature, with mild stirring and under an inert atmosphere, a melanin precursor in an aqueous dispersion of comprising spherical wax particles less than 1 μm in size and at least one emulsifying surfactant;
oxidizing and polymerizing said melanin precursor to form an outer layer enveloping each wax particle such that an aqueous dispersion of composite melanin pigment particles is obtained; and
optionally drying said aqueous dispersion of composite melanin pigment particles so as to obtain a powder.

33. A process according to claim 32, wherein said oxidizing step is carried out below the melting point of said spherical wax particles.

34. A process according to claim 33, wherein said oxidizing step is carried out at room temperature.

35. A process according to claim 32, wherein said polymerizing step is carried out in aqueous media by autoxidation in air brought about by vigorous stirring of the wax microdispersion adjusted to a neutral or alkaline pH.

36. A process according to claim 32, wherein said polymerizing step is carried out in the presence of an oxidizing agent selected from hydrogen peroxide, peracids and persalts.

37. A process according to claim 36, wherein said polymerizing step is carried out in the presence of a pH modifier.

38. A process according to claim 32, wherein said polymerizing step is carried out in the presence of an oxidizing agent selected from alkaline chlorites, silver oxide, ferric chloride, lead oxide, sodium nitrite, rare-earth metal salts, ortho- and para-benzoquinones, ortho- and para-benzoquinone monoimines and diimines, 1,2- and 1,4-naphthoquinones, 1,2- and 1,4-naphthoquinone mono- and diimines.

39. A process according to claim 38, wherein said polymerizing step is carried out in the presence of a pH modifier.

40. A process according to claim 32, wherein said polymerizing step is carried out in using an iodide ion in the presence of hydrogen peroxide.

41. A process according to claim 40, wherein said polymerizing step is carried out in the presence of a pH modifier.

42. A process according to claim 32, wherein said polymerizing step is carried out by enzymatic oxidation.

43. A process according to claim 32, further including the step of incorporating a nonionic amphiphilic compound with a long polar head into the aqueous wax dispersion before the melanin pigment precursor is dispersed therein.

44. A powder or aqueous dispersion comprising the composite melanin pigment of claim 1.

45. A cosmetic or dermatological composition comprising at least one composite melanin pigment according to claim 1.

46. A cosmetic or dermatological composition according to claim 45 wherein said composition is in the form of a powder or an aqueous dispersion.

47. A composition according to claim 45, in which said composite melanin pigment is present in a concentration ranging from 0.1 to 35% by weight, relative to the total weight of the composition.

48. A composition according to claim 47, in which said composite melanin pigment is present in a concentration ranging from 0.5 to 20% by weight, relative to the total weight of the composition.

49. A method of making a make-up product for the skin and/or exoskeleton, said method comprising adding a composite melanin pigment according to claim 1 to said product.

50. A method according to claim 49, wherein said composite melanin pigment is in the form of a powder or an aqueous dispersion.

51. A method of making a dye composition for the hair, said method comprising adding a composite melanin pigment according to claim 1 to said composition.

52. A method according to claim 51, wherein said composite melanin pigment is in the form of a powder or an aqueous dispersion.

53. A method according to claim 51, wherein said dye composition temporarily dyes or makes up the hair.

54. A method of making a composition for protecting the human epidermis and/or the exoskeleton against the harmful effects of UV rays, said method comprising adding a composite melanin pigment according to claim 1 to said composition.

55. A method according to claim 54, wherein said composite melanin pigment is in the form of a powder or an aqueous dispersion.

56. A method according to claim 54, wherein said composition is an antisun product.

57. A method of making a composition for protecting the skin and/or the exoskeleton against the effects of free radicals induced by atmospheric pollutants and/or by ultraviolet radiation, said method comprising adding a composite melanin pigment according to claim 1 to said composition.

58. A method according to claim 57, wherein said composite melanin pigment is in the form of a powder or an aqueous dispersion.

59. A process for the preparation of a composite melanin pigment according to claim 1, said process comprising:

dispersing and solubilizing a melanin precursor in an aqueous dispersion comprising spherical wax particles less than 1 $\mu$m in size and at least one emulsifying surfactant; and oxidizing and polymerizing said melanin precursor to form an outer layer enveloping each wax particle.

* * * * *